United States Patent
Naaman

(10) Patent No.: US 10,397,432 B2
(45) Date of Patent: Aug. 27, 2019

(54) SYSTEM AND METHOD FOR EXTRACTING PRESCRIPTION INFORMATION AND INSTRUCTIONS FROM A LABEL

(76) Inventor: Laith Naaman, Cupertino, CA (US)

(*) Notice: Subject to any disclaimer, the term of this patent is extended or adjusted under 35 U.S.C. 154(b) by 2063 days.

(21) Appl. No.: 13/573,247

(22) Filed: Mar. 27, 2011

(65) Prior Publication Data
US 2013/0182295 A1    Jul. 18, 2013

(51) Int. Cl.
  G06K 19/00  (2006.01)
  H04N 1/04   (2006.01)
  G06F 19/00  (2018.01)
  G06Q 50/22  (2018.01)

(52) U.S. Cl.
  CPC .......... H04N 1/04 (2013.01); G06F 19/3462 (2013.01); A61J 2205/30 (2013.01); A61J 2205/70 (2013.01); G06Q 50/22 (2013.01)

(58) Field of Classification Search
  USPC ....... 235/375, 381, 383, 435, 439, 454, 462; 705/5, 35–45
  See application file for complete search history.

(56) References Cited

U.S. PATENT DOCUMENTS

| | | | | |
|---|---|---|---|---|
| 5,774,865 | A  * | 6/1998  | Glynn   | 705/2 |
| 6,588,869 | B1 * | 7/2003  | Batra   | B41J 29/02 |
| | | | | 347/108 |
| 2005/0252973 | A1 * | 11/2005 | Itoh    | G01N 35/04 |
| | | | | 235/462.01 |
| 2009/0073503 | A1 * | 3/2009  | Lebaschi | H04N 1/00326 |
| | | | | 358/450 |

OTHER PUBLICATIONS

English translation of JP 2009-134657.*

* cited by examiner

Primary Examiner — Matthew Mikels
(74) Attorney, Agent, or Firm — Polsinelli

(57) ABSTRACT

Systems and methods for extraction of prescription information from a medicine bottle are provided. Relevant prescription information and instructions are extracted by imaging or scanning the surface of the medicine bottle, along with spoken instructions based on the extracted information/instructions, are stored in a medicine bottle with an attachment or a storage device. A database of prescription labels used by various pharmacies is used to detect and parse text from the assembled image made of the several scans or images of the bottle.

15 Claims, 1 Drawing Sheet

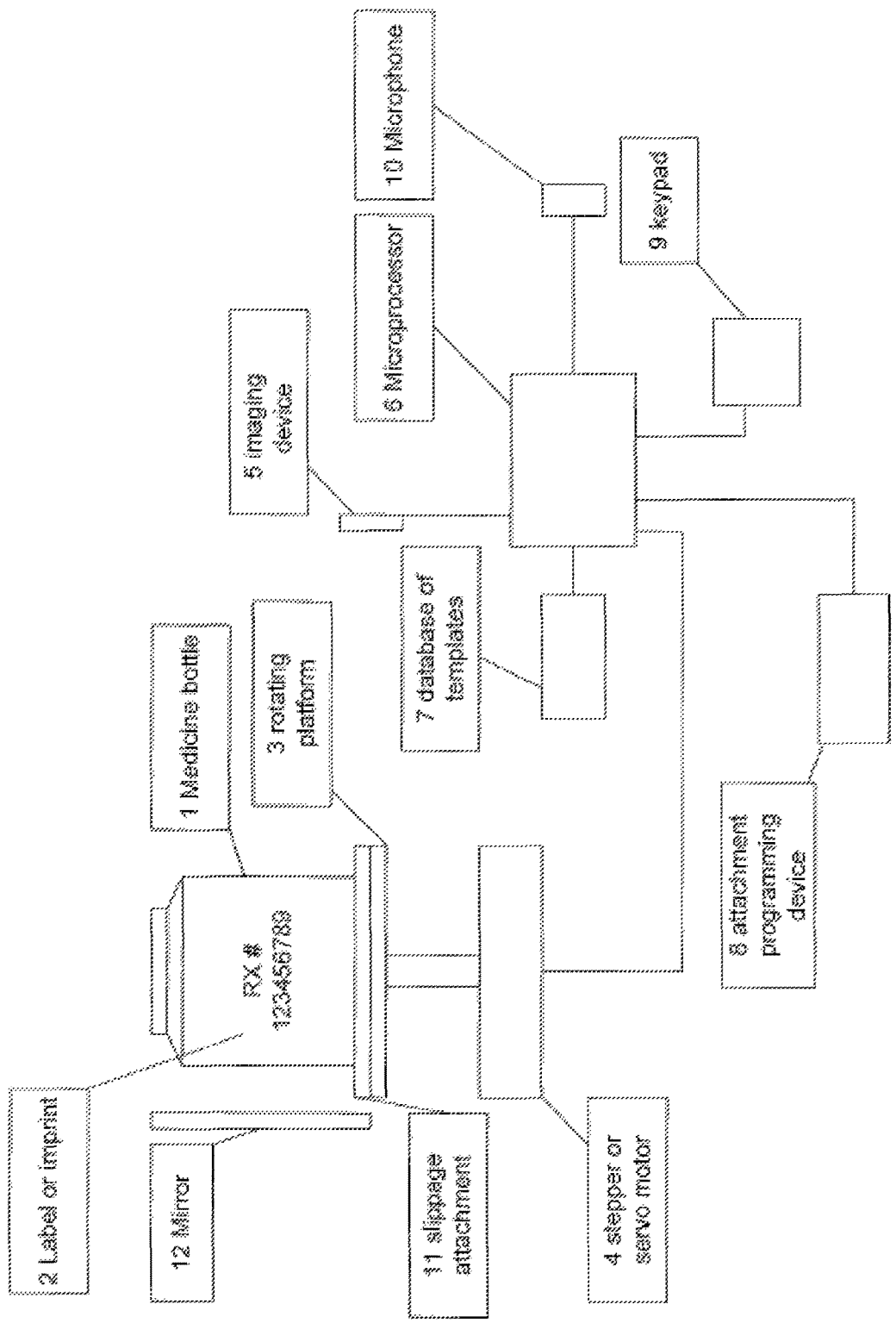

SYSTEM AND METHOD FOR EXTRACTING PRESCRIPTION INFORMATION AND INSTRUCTIONS FROM A LABEL

TECHNICAL FIELD

The present invention relates generally to assistive technology for people who have a full or complicated medication schedule. There are systems and methods to remind such individuals when to take their medication by sounding an alarm, playing back recorded audio instructions, such as dose and possible side effects, generating a notification as to when was the last time a particular medication was taken, and so forth. This information may need to be entered into the system by a caregiver such as a doctor or a pharmacist. This manual entry of the prescription information and instruction may not always be possible. The present invention enables the extraction of prescription information and instructions printed on the medicine bottle or on a label affixed to the said bottle.

BACKGROUND

Many products and/or inventions were introduced to help the elderly or disabled, living independently or with minimal supervision, with their daily routines (e.g., personal hygiene, eating, mobility, and taking medications). According to a study by the Center for Disease Control (CDC) conducted in 2008, there are over 1.3 million legally blind persons in the United States. Blindness and irreversible visual impairment cost the federal government more than $4 billion annually. In addition, one in 8 Americans is over the age of 65, and almost half of them (6%) are over the age of 75. According to the US Department of Health and Human Services Administration on Aging, in 2000 there were 10 million Americans over the age of 65 living alone; almost half of them have sensory disability. One common disability among the elderly especially over 75 years of age is the loss of vision either due aging or to other diseases common to the elderly, such as diabetes.

Such people may need help in their daily routines, especially if they were living independently, and one such routine is keeping track of their medications. It is not uncommon for people in the 75+ age group or even younger to be taking a number of medications on a daily basis and need help keeping track of their medications through sensory alarms such as audio, vibrating, and visual alarms. On occasions, the users may not be within perception range of the alarm, so a wireless alarm may also be used to attract their attention.

The information, whether data in digital form or information/instructions in audio form, may have to be entered manually. In some cases, either the doctor or the pharmacist may not be available to spend the extra time to program the instructions.

What is needed is a system that can automatically extract prescription information from medicine bottles, whether printed on the bottles or on labels and enter that information to program various assistive tools related to medication.

DESCRIPTION

Embodiments of the present invention provide a system and method for extracting prescription information and instructions from a medicine bottle, to a form usable for storage and processing. The information regarding a prescription may include a prescription number, name of the user, name of the medication, quantity, strength, and dose. Such information may be extracted from the medicine bottle or a label affixed to it and stored on an attachment external to a medicine bottle. Additionally, an audio message containing the name of the user, the purpose of the medication (e.g., blood pressure, heart condition, etc.), dose, and any possible side effects or necessary precautions may be generated and recorded on the attachment. The medicine bottle with the attachment may be inserted in a medication management and monitoring unit which may accept several such bottles, and the information in the attachment may be read into the unit. The medication information can be entered to the attachment using a computing device, an interface, or a keypad. Such input devices may communicate with the unit through a wired or wireless connection as known in the art.

The system may include a scanning or imaging device that scans the surface of the medication bottle; a rotating platform, an attachment that attaches to the medicine bottle from one side and to the rotating platform from the other to prevent slippage, a microprocessor that assembles the scans or images into one image, parses the image for text, and decodes the information. A database of templates of the prescription labels of various pharmacies may be used in the decoding and information extraction from the medicine bottle. Such templates may include information where to find the different components of a prescription such patient's name, name of medication, etc. The unit can include an illumination device such as LED and a rotating platform.

When a patient inserts a medicine bottle in the unit, he or she can speak his or her name into a microphone, enter a pharmacy code from a list into the keypad, and then push the start button. The unit controlled by the microprocessor may then scan the surface of the medicine bottle taking several snap shots which are assembled into one image. The microprocessor can analyze the assembled image for text using the corresponding stored template in the database and parses the detected text for information and instructions.

The patient may then insert the medicine bottle with an attachment to hold the prescription information in the unit. The relevant information may then be programmed on an attachment to be attached to the medicine bottle, additionally, audio messages stored in the microprocessor or in an external storage corresponding to the instructions imprinted on the medicine bottle or the label affixed to it, may be recorded (programmed) on the attachment.

DESCRIPTION OF FIGURE

FIG. 1 depicts one embodiment of the system for prescription information extraction from a medicine bottle 1: medicine bottle
2: Label or imprint of the prescription information and instructions.
3: Rotating platform to rotate the medicine bottle to enable scanning the entire surface of the medicine bottle.
4: A stepper or a servo motor to rotate the medicine bottle.
5: An imaging or a scanning device controlled by the microprocessor [6].
6: Microprocessor to control, capture and process captured information.
7: A database of templates of the prescription labels or imprints of various pharmacies.
8: One embodiment of the attachment sensing and programming device.
9: Keypad to enter pharmacy code.
10: Microphone.

11: slippage attachment, a small attachment that prevents slippage of the bottle when the platform under it rotates.

What is claimed is:

1. A system for extracting prescription information from a medicine bottle, the system comprising:
    a platform that supports and rotates the medicine bottle;
    a mirror that reflects an outer surface of the medicine bottle as the medicine bottle is rotated;
    an imaging device that captures a plurality of snapshots of the reflected outer surface of the medicine bottle as the medicine bottle is rotated;
    a microprocessor that:
        assembles the captured plurality of snapshots into a single image;
        detects text in the assembled single image, and
        parses the detected text to identify a patient name and a medication name;
    a keypad used to enter a digital pharmacy code for a dispensing pharmacy of the medicine bottle; and
    a microphone that records an audio reading of information to be associated with the medicine bottle.

2. The system of claim 1, further comprising storage that stores a plurality of recorded audio messages.

3. The system of claim 1, further comprising a database that stores information regarding a plurality of dispensing pharmacies label templates, wherein a selected template is used to parse the text detected in the assembled single image.

4. The system of claim 1, wherein the prescription information is selected from the group consisting of prescription number, the patient name, medication information, medication name, dose, quantity, frequency, side effects, warnings, and directions.

5. The system of claim 1, further comprising an attachment sensing and programming device.

6. The system of claim 1, further comprising memory that stores prescription information as text or audio on an medicine bottle attachment.

7. The system of claim 1, further comprising an illumination source.

8. The system of claim 7, wherein the illumination source is an light-emitting diode (LED).

9. The system of claim 3, wherein the selected template specifies where to find the patient name and the medication name.

10. A method for extracting prescription information from a medicine bottle, the method comprising:
    rotating the medicine bottle on a platform;
    reflecting an outer surface of the medicine bottle in a mirror as the medicine bottle is rotated;
    capturing a plurality of snapshots of the reflected outer surface of the medicine bottle as the medicine bottle is rotated; and
    executing instructions stored in memory, wherein execution of instructions by a microprocessor:
        assembles the captured plurality of snapshots into a single image;
        detects text in the assembled single image, and
        parses the detected text to identify a patient name and a medication name.

11. The method of claim 10, wherein parsing the detected text is based on a selected template that specifies where to find the patient name and the medicine name.

12. The system of claim 1, wherein the captured plurality of snapshots are of multiple different portions on multiple different sides of the outer surface of the medicine bottle, and wherein the single image assembled by the microprocessor from the plurality of captured snapshots is a combination of the different portions on the different sides.

13. The system of claim 12, wherein the multiple different portions on the multiple different sides constitute an entirety of the outer surface of the medicine bottle.

14. The system of claim 3, wherein the microprocessor further decodes the parsed text based on one of the label templates.

15. The system of claim 14, wherein the label template specifies where each label component is located within the label template, each label component corresponding to a different type of information.

* * * * *